United States Patent [19]

Toda et al.

[11] Patent Number: 5,262,431
[45] Date of Patent: Nov. 16, 1993

[54] PROLINAL DERIVATIVES AND PHARMACEUTICAL COMPOSITIONS THEREOF

[75] Inventors: Masaaki Toda, Osaka; Shuichi Ohuchida, Kyoto; Hiroyuki Ohno, Shiga, all of Japan

[73] Assignee: Ono Pharmaceutical Co., Ltd., Osaka, Japan

[21] Appl. No.: 836,971

[22] Filed: Feb. 19, 1992

Related U.S. Application Data

[62] Division of Ser. No. 536,830, Jun. 12, 1990, Pat. No. 5,112,847, which is a division of Ser. No. 139,231, Dec. 29, 1987, Pat. No. 4,983,624.

Foreign Application Priority Data

Dec. 29, 1986 [JP] Japan ................ 61-310151

[51] Int. Cl.$^5$ ............... A61K 31/40; C07D 213/24
[52] U.S. Cl. ................... 514/343; 514/224.8; 514/397; 514/414; 514/422; 544/35; 544/37; 546/281; 548/314.7; 548/467; 548/525; 548/527; 548/530; 548/540
[58] Field of Search ............. 548/540, 530, 314.7, 548/467, 525, 527; 546/281; 514/423, 343, 224.8, 397, 414, 422; 544/35, 37

[56] References Cited

U.S. PATENT DOCUMENTS

| 4,701,465 | 10/1987 | Tanaka et al. | 514/423 |
| 4,956,380 | 9/1990 | Toda et al. | 514/422 |

FOREIGN PATENT DOCUMENTS

| 0172458 | 2/1986 | European Pat. Off. |
| 0201742 | 11/1986 | European Pat. Off. |
| 0201743 | 11/1986 | European Pat. Off. |

*Primary Examiner*—Joseph P. Brust
*Assistant Examiner*—Jacqueline Haley
*Attorney, Agent, or Firm*—Sughrue, Mion, Zinn, Macpeak & Seas

[57] ABSTRACT

A novel prolinal derivative of general formula:

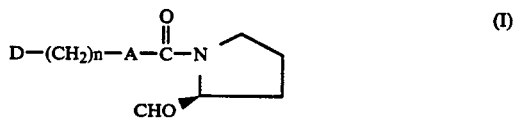

[wherein A represents a group of the general formula:

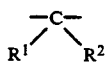

(wherein one of $R^1$ and $R^2$ represents hydrogen atom and the other represents alkyl group of from 2 to 5 carbon atoms, alkoxy group of from 1 to 5 carbon atom(s), phenyl group, benzyl group, cycloalkyl group of from 4 to 6 carbon atoms or (cycloalkyl group of from 4 to 6 carbon atoms)—methyl group or $R^1$ and $R^2$ each represents, same or different, alkyl group of from 1 to 4 carbon atom(s).) or a group of the general formula:

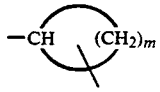

(wherein m represents an integer of from 3 to 6.)
n represents an integer of from 3 to 10.
D represents carbocyclic or heterocyclic ring unsubstituted or substituted by from one to three of halogen atom, nitro group, trifluoromethyl group, alkyl or alkoxy group of from 1 to 4 carbon atom(s).]

possess inhibitory activity on prolyl endopeptidase, and therefore be useful for treating and/or preventing agent for amnesia.

7 Claims, No Drawings

PROLINAL DERIVATIVES AND PHARMACEUTICAL COMPOSITIONS THEREOF

This is a divisional of application Ser. No. 07/536,830 filed Jun. 12, 1990, U.S. Pat. No. 5,112,847 is a divisional of prior application Ser. No. 07/139,231 filed Dec. 29, 1987 (now U.S. Pat. No. 4,983,624).

SUMMARY

This invention is related to novel compounds having an inhibitory activity on prolyl endopeptidase.

More particularly, this invention is related to
1) Novel prolinal derivatives having an Inhibitory activity on prolyl endopeptidase, of the following general formula:

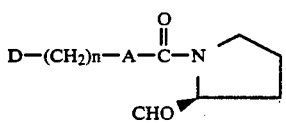

(I)

[wherein all of the symbols are the same meaning as hereafter defined.]
2) process for the preparation of them, and
3) anti-amnesia agent containing them as active ingredient.

BACKGROUND

Recent advance in neuroscience is making clear the natural shape of neurotransmitters, substances deeply related memory in the brain. It is said that some of these substances are neuropeptides containing prolines.

Recovery of the memory was reported by the dose of neuropeptide containing proline to an experimental amnesia rat (See Science 211, 601 (1981)). on the other hand, it is presumed that these neuropeptide-hormones shall be metabolized by cerebral endogenous peptidases. Especially, prolyl endopeptidase (EC, 3. 4. 21. 26) might take part in this metabolism closely (See J. Biochem., 94, 1179 (1983)).

From these facts, the studies were in progress that it should be possible to prevent or treat amnesia by inhibiting prolyl endopeptidase and suppressing the metabolism of neutrotransmittes. (See Protein, Nucleic acid and Enzyme 25(6), 513(1980); Nippon Nougei Kagaku Kaishi 58(11), 1147(1984); J. Neurochem., 41, 69(1983); ibid 42, 237(1984).)

For the purpose described above, several compounds were synthesized. For example, it is clear that N-benzyloxycarbonyl-glycyl-L-prolyl-chloromethane and N-benzyloxycarbonyl-L-prolyl-prolinal strongly inhibit prolyl endopeptidase (See J. Neurochem., 41, 69 (1983)). More recently, it is disclosed that compounds shown below are effective for the above purpose.

(i) Prolinal derivatives of general formula:

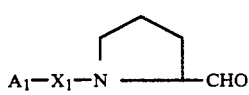

(A)

[wherein $A_1$ represents a protecting group of amino acid group in the field of amino acid chemical, and $X_1$ represents a residual group of amino acid.] (See Japanese Patent Kokai No. 60-188317, i.e. European Patent Publication No. 154353).

(ii) N-acylpyrrolidine derivatives of general formula:

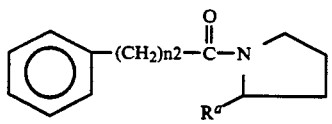

(B)

wherein n2 represents a number of 1~4, and $R^a$ represents lower alkyl ester group, —CH$_2$OH group or aldehyde group.] (See Japanese Patent Kokai No. 61-37764; a compound wherein n2 is 5 is also disclosed by correction, i.e. European Patent Publication No. 172458).

(iii) Compounds of general formula:

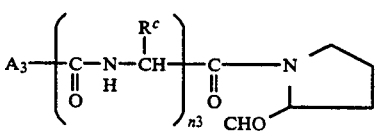

(C)

[wherein $A_3$ represents methyl group or benzyloxy group, $R^c$ represents isopropyl group or isobutyl group on condition that plural R's have the same meaning in one formula. And n3 represents 2 or 3.] (See Japanese Patent Kokai No. 61-183297.)

Most recently, five applications related to anti-amnesia agents having prolinal skeltons were published. i.e.

(iv) Compounds of general formula:

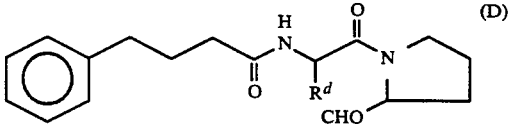

(D)

(wherein $R^d$ represents a group of —CH$_3$,

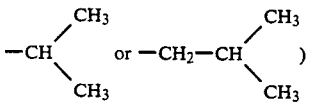

)

(See Japanese Patent Kokai No. 61-238775, i.e. European Patent Publication No. 201741).

(v) N-acylpyrrolidine derivatives of general formula:

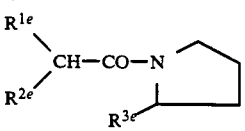

(E)

[wherein $R^{3e}$ represents lower alkyloxycarbonyl group, hydroxymethyl group or formyl group, $R^{1e}$ represents a hydrogen atom or lower alkyl group, $R^{2e}$ represents phenyl group or d group of the following formula:

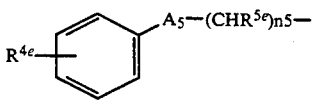

(wherein $R^{4e}$ represents a hydrogen atom, a halogen atom or lower alkoxy group, $R^{5e}$ represents a hydrogen atom or lower alkyl group, n5 represents 0 or 1, $A_5$ represents an oxygen atom, methylene group, hydroxymethylene group, phenylmethylene group or carbonyl group.) or $R^{1e}$ and $R^{2e}$ represent, together with, benzylidene group unsubstituted or substituted on its aromatic ring(s).] (See Japanese Patent Kokai No. 61-238776, i.e. European Patent Publication No. 201742).

(vi) Compounds of general formula:

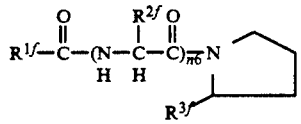
(F)

[wherein n6 represents a number of 0~2. $R^{1f}$ represents a straight-chained organic group of from 5 to 25 carbon atoms which is saturated or unsaturated wherein an carbon chain may contain plural number of double bonds. $R^{2f}$ represents a group of

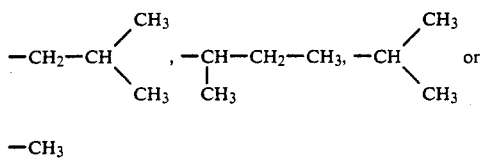

$-CH_3$ $R^{3f}$ represents lower alkyl ester group, $-CH_2OH$ group or aldehyde group.] (See Japanese Patent Kokai No. 61-238799, i.e. European Patent Publication No. 201743).

(vii) Compounds of general formula:

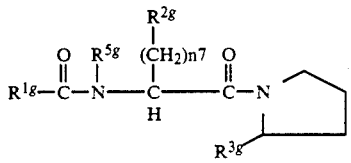
(G)

(wherein n7 is an integer of more than one, $R^{1g}$ is a saturated or unsaturated straight-chained hydrocarbon group of from 5 to 25 carbon atoms. Herein said unsaturated carbon chain may contain plural number of double bonds. $R^{3g}$ represents lower alkyl ester group of the formula: $-COOR^{4g}$ (wherein $R^{4g}$ represents lower alkyl group.), hydroxymethyl group or formyl group, $R^{2g}$ represents methyl group, phenyl group, hydroxyphenyl group, indolyl group, imidazolyl group, carboxyl group, fermyl group, amino group, hydroxy group, hydroxyalkyl group, thiol group, methylthio group or guanidino group etc. and each of above groups may be substituted. $R^{5g}$ represents a hydrogen atom or a single bond between carbon atom and nitrogen atom together with $R^{2g}$ when n7 is 3.) (See Japanese Patent Kokai No. 62-84058, i.e. European Patent Publication No. 201743).

(viii) Dipeptide derivatives of general formula:

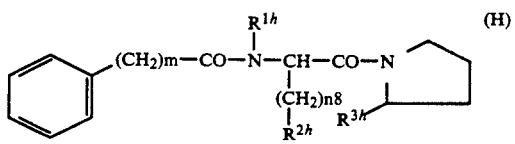
(H)

(wherein m represents an integer of 1~8, n8 represents an integer of 1~6, $R^{1h}$ represents a hydrogen atom, $R^{2h}$ represents a hydrogen atom, a branched alkyl group of from 3 to 5 carbon atoms, phenyl group, hydroxyphenyl group, indolyl group, imidazolyl group or methylthio group, or a single bond between carbon atom and nitrogen atom with $R^{1h}$. $R^{3h}$ represents lower alkyl ester group, hydroxymethy group or formyl group.) (See Japanese Patent Kokai No. 62-148467, i.e. European Patent Publication No. 201741).

And more, the present inventors have filed an application related to prolinal derivatives having an activity of anti-amnesia, in advance of the present application, i.e.

(ix) Prolinal derivatives of general formula:

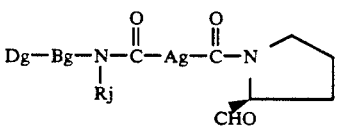
(J)

[wherein $A_9$ represents alkylene or alkenylene group of from 1 to 8 carbon atom(s) or a saturated hydrocarbon ring of from 3 to 7 carbon atoms, $R^j$ represents hydrogen atom, phenyl group, benzyl group, alkyl group of from 1 to 8 carbon atom(s) or cycloalkyl group of from 3 to 7 carbon atoms, Bg represents alkylene group of from 1 to 8 atom(s) unsubstituted or substituted by phenyl group or benzyl group or a single bond, $D_9$ represents carbocyclic or heterocyclic ring unsubstituted or substituted by from one to three of halogen atom, alkyl or alkoxy group of from 1 to 4 carbon atom(s), nitro group or trifluoromethyl group.] (See European Patent Application filed on 10th November, 1987.)

COMPARISON WITH THE PRIOR ARTS

The compounds of the present invention of the general formula (I) are prolyl endopeptidase inhibitors having the same prolinal (i.e. pyrrolidin-2-al) skelton as compounds described hereinbefore of the general formulae of from (A) to (J) and compounds shown in the literature, i.e. J. Neurochem., 41.

But, the compounds of the present invention are novel and remarkably different compounds in structure and activity from the compounds cited hereinbefore.

That is to say, the compounds shown in (A), (C), (0), (F), (G) and (H), and In the literature, i.e. J. Neurochem., 41 have structures that amine acid is attached to the nitrogen atom of prolinal, and are remarkably different in structure from the compounds of the present invention. On the other hand, the compounds shown in (B) and (E) have structures that alkanoyl group is attached to the nitrogen atom of prolinal. For example, among the compounds shown in (E), the general formula of the compounds wherein $R^{1e}$ is lower alkyl group, $R^{3e}$ is formyl group, $R^{4e}$ is hydrogen atom, halogen atom or lower alkoxy group, $R^{5e}$ is hydrogen atom, $A^5$ is methylene group and n5 is one is follows:

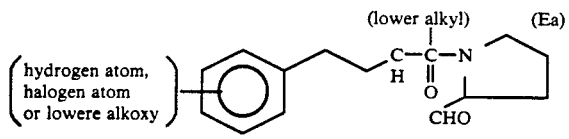

The compounds of the present invention are the compounds that a group of

(wherein m represents the same meaning as hereinbefore defined) is introduced In place of (lower alkyl-CH)
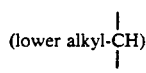

in the compound (Ea) or cycloalkyl group, phenyl group and benzyl group are introduced in place of (lower alkyl) group in the compound (Ea). So, the compounds of the present invention can be said to be remarkably different from the compounds shown in (B) or (E) in structure.

Moreover, it was confirmed that the compounds of the prevent invention obtained by elongating alkylene chain between substituent phenyl group and (lower alkyl-CH)
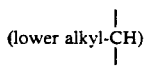

in the compound of the general formula (Ea) have superior effect (inhibitory activity on prolyl endopeptidase) to the compounds shown in the general formula (Ea).

And we, the present inventor, have confirmed in the previous application (compounds represented by the general formula (J)) that compounds wherein benzene ring was replaced by other aromatic rings including heterocyclic rings and saturated rings, e.g. naphthalene, fluorene, furan rings) have also maintained the inhibitory activity on prolyl endopeptidase in the results of several modification in D.

Among the compounds of the present invention which are the compounds modified the compounds of the general formula (J) in the parts other than D, it is not difficult to forecast that the compounds wherein D was replaced by the other rings should have maintained the activity, If the compounds wherein D is benzene ring have enough activity.

DISCLOSURE OF THE INVENTION

The present invention is related to
1) A novel prolinal derivative of the general formula:

[wherein A represents a group of the general formula:

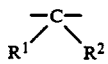

(wherein one of $R^1$ and $R^2$ represents hydrogen atom and the other represents alkyl group of from 2 to 5 carbon atoms, alkoxy group of from 1 to 5 carbon atom(s), phenyl group, benzyl group, cycloalkyl group of from 4 to 6 carbon atoms or (cycloalkyl group of from 4 to 6 carbon atoms)—methyl group or $R^1$ and $R^2$ each represents, same or different, alkyl group of from 1 to 4 carbon atom(s).) or a group of the general formula:

(wherein m represents an integer of from 3 to 6.) n represents an integer of from 3 to 10. D represents carbocyclic or heterocyclic ring unsubstituted or substituted by from one to three of halogen atom, nitro group, trifluoromethyl group, alkyl or alkoxy group of from I to 4 carbon atom(s).]

2) Process for the preparation of them and

Anti-amnesia agent containing them as active ingredient.

The terms of alkyl group and alkoxy group each symbol throughout the present specification including claims mean straight-chain or branched-chain alkyl group and alkoxy group.

In the structural formulae throughout the present specification dashed lines (——) indicate α-configuration, tapered lines indicate β-configuration, wavy lines indicate α- or β-configuration or mixture thereof.

In the general formula (I), alkyl groups of from 2 to 5 carbon atoms represented by $R^1$ or $R^2$ are ethyl, propyl, butyl, pentyl and isomeric groups thereof.

In the general formula (I), alkoxy groups of from 1 to 5 carbon atom(s) represented by $R^1$ or $R^2$ are methoxy, ethoxy, propoxy, butoxy, pentyloxy and isomeric groups thereof.

In the general formula (1), cycloalkyl groups of from 4 to 6 carbon atoms and cycloalkyl groups of from 4 to 6 carbon atoms in (cycloalkyl groups of from 4 to 6 carbon atoms) - methyl groups represented by $R^1$ or $R^2$ are cyclobutyl, cyclopentyl and cyclohexyl.

In the general formula (I), alkyl groups of from 1 to 4 carbon atom(s) represented by $R^1$ and $R^2$ and alkyl groups of from 1 to 4 carbon atom(s) in D are methyl, ethyl, propyl, butyl and isomeric groups thereof.

In the general formula (I), the general formula: $—(CH_2)_n—$, which represents straight-chain alkylene group of from 3 to 10 carbon atoms, means trimethylene, tetramethylene, pentamethylene, hexamethylene, octamethylene, nonamethylene, or decamethylene group.

In the general formula (I), the general formula:

which represents saturated hydrocarbon rings of from 4 to 7 carbon atoms, means cyclobutane, cyclopentane, cyclohexane or cycloheptane ring.

In the general formula (I), alkoxy groups of from 1 to 4 carbon atom(s) in D are methoxy, ethoxy, propoxy, butoxy and isomeric groups thereof.

In the general formula (I), halogen atoms in D are florine, chlorine, bromine, and Iodine atoms.

In the general formula (I), preferable A is the case wherein $R^1$ is hydrogen atom and $R^2$ is isopropyl or isobutyl group, wherein both of $R^1$ and $R^2$ are methyl groups, or the case that A is cyclopentane or cyclohexane ring.

In the general formula (I), preferable n is 5, 6, 7 or 8.

In the general formula (I), carbocyclic ring represented by D means mono-, bi- or tri-cyclic aromatic carbocyclic ring(s) containing not more than 15 carbon atoms which may be partially or fully saturated.

Examples of the rings mentioned above are benzene, naphthalene, indene, azulene, fluorene, phenanthrene, anthracene, acenaphthalene, biphenylene rings and partially or fully saturated rings thereof.

In the general formula (I), heterocyclic ring represented by D means mono-, bi- or tri-aromatic heterocyclic ring(s) containing not more than 15 carbon and hetero atoms which may be partially or fully saturated. In above heterocyclic rings, rings containing one or two of hetero atom(s) are preferred.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoendole, benzofuran, benzothiophene, indolizine, chromene, quinoline, isoquinoline, quinolizine, purine, indazole, quinazoline, cinnoline, quinoxaline, phthalazine, pteridine, carbazole, acridine, phenanthridine, xanthene, phenazine, phenothiazine rings and partially or fully saturated rings thereof.

In the general formula (I), preferred rings represented by D especially are benzene, naphthalene, fluorene, pyridine, furan and acridine rings and partially saturated rings thereof.

In the above rings, substituted benzene rings are preferred as substituted rings by substituent(s).

Throughout the specification including claims, stereo isomers generated by stereo configuration(s) (asymmetric carbon, double bond etc.) and structural isomers generated by branch of a carbon chain, etc., are included in the present invention.

Process for the Preparation

According to the present invention, the compounds of the present Invention of the general formula (I) may be prepared by oxidizing a compound of general formula:

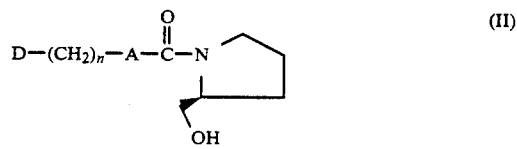

[wherein all of the symbols are the same meanings as hereinbefore defined.] in a mild condition.

Oxidation in a mild condition is known and may be carried out, for example, using an oxidation agent (sulfur trioxide-pyridine complex, chromium trioxide-pyridine complex, t-butyl chloroformate, oxalyl chloride etc.), with a tertiary amine (triethylamine, pyridine etc.) or without, in an inert organic solvent (DMSO, methylene chloride, chloroform, benzene etc.), at a temperature of from 0° C. to 50° C.

Process for the Preparation of Intermediates

Prolinol derivatives of the general formula (II) may be prepared by the series of reactions shown in the following scheme [A].

Scheme [A]

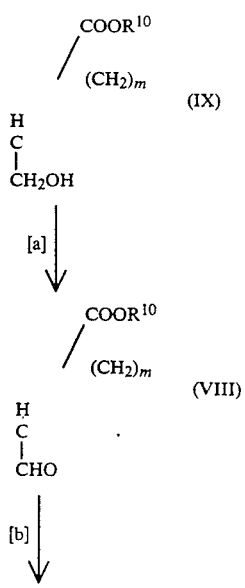

Scheme [A]

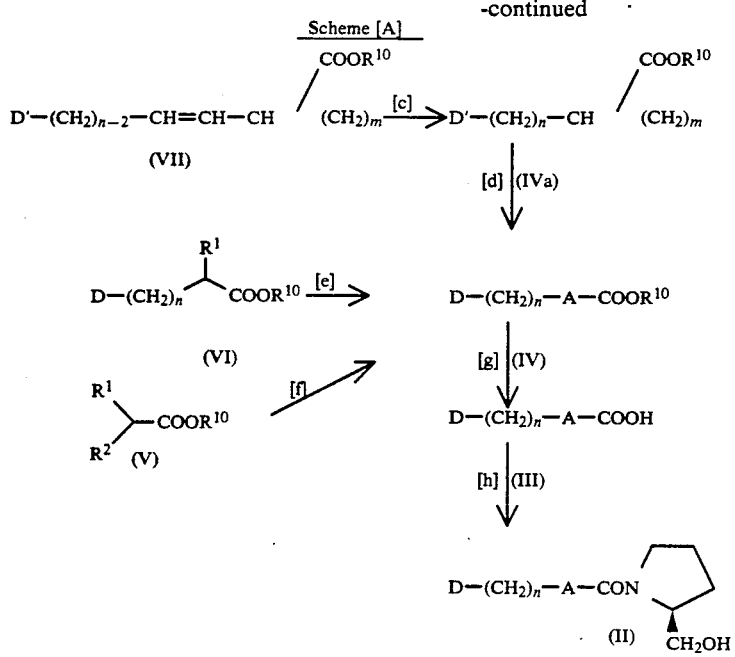

Each symbol in the reaction scheme [A] represents the following meanings or the same meanings as hereinbefore defined.

- D'—carbocyclic or heterocyclic ring unsubstituted or substituted by from one to three of halogen atom, trifluoromethyl group, alkyl or alkoxy group of from 1 to 4 carbon atom(s),
- $R^{10}$—alkyl group of from 1 to 4 carbon atom(s) or hydrogen atom,
- m—an integer of from 3 to 6.

Each reaction step in the scheme [A] is described in the following.

Step [a] is oxidation, and known reaction, and it may be carried out, for example, by the method described hereinbefore.

Step [b] is Wittig's reaction, and known reaction, and it may be carried out, for example, by reacting the corresponding Wittig's reagent (for example, the general formula:

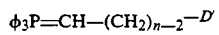

$$\phi_3P=CH-(CH_2)_{n-2}-D'$$

(wherein all of the symbols represent the same meaning as hereinbefore defined.)) and the compound of the general formula (VIII) in an inert organic solvent (DMSO, ethyl ether, tetrahydrofuran, chloroform, benzene etc.) at from −78° C. to room temperature.

Step [c] is reduction, and known reaction, and it may be carried out, for example, in an atmosphere of hydrogen, in a organic solvent (methanol, ethanol, tetrahydrofuran, ether etc.) and in the presence of a catalyst (palladium-carbon, palladium, platinum black, nickel etc.) at a temperature of from 0° C. to 40° C.

In to step [d], the compound of the general formula (IVa) may be nitrized if desired. Nitration is known reaction, and it may be easily carried out, for example, by using ordinary nitration reagent, such as a mixture of nitric acid and sulfuric acid, nitric acid in acetic acid or nitric acid and sulfuric acid in acetic acid etc.

Step [e] is carried out that a lithioated compound which is obtained by reacting a compound of the general formula (VI) and a lithiating agent (lithium diisopropyl amide etc.) in an inert organic solvent (tetrahydrofuran, diethyl ether, hexamethylphosphoramide (HMPA), hexane, pentane or a mixture solvent containing two or more of them) at from −78° C. to room temperature is reacted with the halogenide of the general formula:

$$R^2-X \quad (X)$$

(wherein $R^2$ represents the same meaning as hereinbefore and X represents bromine atom or iodine atom.)

Step [f] is Curried out that a lithioated compound which is obtained by reacting a compound of the general formula (V) and a lithioated compound (lithium diisopropyl amide etc.) by the same procedure as step [e] is reacted with a halogenide compound of the general formula:

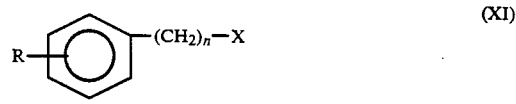

(XI)

(wherein all of the symbols represent the same meaning as hereinbefore defined.).

Step [g] is saponification, which Is carried out in only the case that $R^{10}$ represents lower alkyl group in the general formula (IV), and known reaction, for example, using an aqueous solution of alkali (sodium hydroxide, potassium hydroxide etc.) in alkanol (ethanol, methanol etc.).

Among the compounds of the general formula (III), the compounds wherein R represents a group except hydrogen atom (as R") are obtained by introducing R" into the compounds wherein R is hydrogen atom. For example, the compounds wherein R" is nitro group may be obtained by nitration as step [d].

Step [h] is the reaction to form amide bond. For example, it may be carried out by reacting 2-hydroxymethylpyrrolidine indicated by the formula:

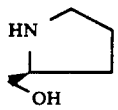

and a carboxylic acid indicated by the general formula (III).

Reactions to form amide bond with a carboxylic acid and an amine are known and, for example, are
① method using an acid halide
② method using a mixed acid anhydride
③ method using DCC etc.

Described concretely, ① Method using an acid halide, for example, may be carried out by reacting an amine of the general formula (IIa) and an acid halide obtained by reacting a carboxylic acid of the general formula (III) and an acid halide (oxalyl chloride, pivaloyl chlori ionyl chloride, tosyl chloride, mesyl chloride etc.) In an inert organic solvent (chloroform, methylene chloride, diethyl ether, THF etc.) or without solvent at from −20° C. to the reflux temperature, in the presence or absence of a base, for example, tertiary amine (triethylamine, pyridine, picoline etc.) in an inert organic solvent (as hereinbefore described), at d temperature of from −5° C. to 40° C.

② Method using d mixed acid anhydride may be carried out, for example, by reacting a mixed acid anhydride obtained by reacting a carboxylic acid of the general formula (III) and an acid halide (as hereinbefore described) or an acid derivative (ethyl chloroformate, isobutyl chloroformate etc.) in the presence of a tertiary amine (as hereinbefore described) in an inert organic solvent (as hereinbefore described) or without solvent at a temperature of from 0° C. to 40° C., and an amine of the general formula (IIa) in an inert organic solvent (as hereinbefore described), at a temperature of from 0° C. to 40° C.

③ Method using DCC may be carried out, for example, by reacting a carboxylic acid of the general formula (III) and an amine of the general formula (IIa) using DCC (dicyclohexylcarbodiimide) in the presence or absence of a tertiary amine (as hereinbefore described), in an inert solvent (as hereinbefore described), at a temperature of from 0° C. to 40° C.

The reactions in ①, ② and ③ hereinbefore are preferred to be carried out in an atmosphere of inert gas (argon, nitrogen etc.) on anhydrous condition.

The raw material compounds of the general formula (IIa), (V), (VI), (IX), (X) and (XI) are known, or may be prepared by known method.

Throughout the specification, in each reaction, products may be purified by conventional methods, For example, distillation at atmosphere or reduced pressure, high performance liquid chromatography, thin layer chromatography using silica gel or magnesium silicate or washing or recrystallization. Purification may be carried out after each reactions or a series of reaction.

PHARMACOLOGICAL ACTIVITIES

The compounds of the present invention of the general formula (I) possess an inhibitory activity on prolyl endopeptidase, described before, for example, in a standard laboratory test, results in the followings are given.

Prolyl Endopeptidase Inhibitory Activity In Vitro

The compounds of the present Invention showed activities as in the following Table I-IV, with the test system described hereafter.

TABLE I

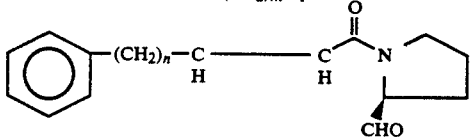

(Ia)

| Example No. of the compounds | Concentration for 50% inhibition $IC_{50}$ (μM) |
|---|---|
| 2 (n = 4, m = 4) | 0.13 |
| 2(a) (n = 3, m = 5) | 0.43 |

TABLE II

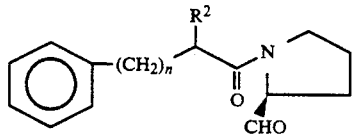

(Ib)

| Example No. of the compounds | Concentration for 50% inhibition $IC_{50}$ (μM) |
|---|---|
| 1(j) (n = 5, $R^2$ = —⟨phenyl⟩) | 0.61 |
| 1(h) (n = 4, $R^2$ = —⟨cyclohexyl⟩) | 0.69 |

TABLE III

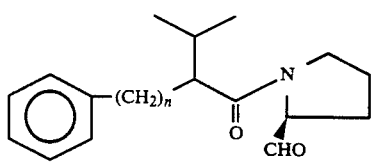

(Ic)

| | Example No. of the compounds | Concentration for 50% inhibition $IC_{50}$ (μM) |
|---|---|---|
| The compounds of the present invention | I(a) (n = 3) | 0.37 |
| | 1 (n = 4) | 0.28 |
| | 1(b) (n = 5) | 0.08 |
| | 1(c) (n = 6) | 0.19 |
| | 1(d) (n = 7) | 0.23 |
| | 1(e) (n = 8) | 0.12 |
| Compared compound | N-(2-isopropyl-4-phenyl-butyryl)-L-prolinal (n = 2)*[1] | >5 |

*[1]The compound described in Specification of Japanese Patent Kokai No. 61-238776 (Compound No. 33)

TABLE IV (Structure Id): CH3O-phenyl-(CH2)n-CH(R²)-C(=O)-N(pyrrolidine)-CHO

| Example No. of the compounds | | Concentration for 50% inhibition IC$_{50}$ (μM) |
|---|---|---|
| The compounds of the present invention | 3 (n = 5, R² = –CH(CH₃)₂) | 0.17 |
| Compared compounds | N-[4-(4-methoxyphenyl)butyryl]-L-prolinal (n = 2, R² = H)*² | 21 |

*²The compound described in Specification of Japanese Patent Kokai No. 61-238776 (Compound No. 9)

Inhibitory activity of prolyl endopeptidase in vitro was measured by the following test system.

A mixed solution of 20 mM tris-HCl buffer (pH 7.5; 935 μl; containing 10 mM EDTA and 10 mM mercaptoethanol), a solution of a compound of the present invention In DMSO (10 μl) and a solution of prolyl endopeptidase which was purified from bovine brain (0.13 unit; prepared by the method described in J. Biochem., 94, 1179 (1983)) in tris-HCl buffer (15 μl) was preincubated for 15 mins at 37° C.

To the solution, 5 mM of N-benzyloxycarbonyl-glycyl-prolyl-p-nitroanilide (40 μl) in a mixture of 40% dioxane-60% water was added. The solution was incubated for 1 min at the same temperature.

Optical absorption ($a_1$) at 405 nm of the solution, and optical absorption ($a_2$) at 405 nm of the solution after more 30 mins' incubation at 37° C. were measured.

Optical absorptions ($b_1$ and $b_2$) of the solutions using DMSO instead of the solution of the compound of the present invention were also measured.

Inhibitory ratio was calculated by the following expression and IC$_{50}$ (required concentration for 50% inhibition) was obtained (See Protein, Nucleic acid and Enzyme 25(6), 513, 1980.).

$$\text{Inhibitory ratio (\%)} = \frac{(b_2 - b_1) - (a_2 - a_1)}{b_2 - b_1} \times 100$$

Toxicity

On the other hand, it was confirmed that the acute toxicity of the compound of the present invention were fully little. Therefore, the prolinal derivatives of the present invention may be considered to be sufficiently safe and suitable for pharmaceutical used.

Application for the Pharmaceuticals

To inhibit prolyl endopeptidase is to suppress the metabolism of neurotransmitter substances taking part in the memory in brain (each of them is peptide) described hereinbefore, and therefore be useful for prevention and/or treatment for amnesia, in animals including human beings, especially human beings.

The compounds of the present invention possess a inhibitory activity on prolyl endopeptidase in vitro, so they are expected to be useful for prevention and/or treatment of amnesia.

For the purpose above described, the compounds of the present invention may normally by administered systemically or locally usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 500 mg, by oral administration, up to several times per day, and between 1 mg and 100 mg, by parenteral administration (preferably, intravenous administration) up to several times per day.

As mentioned above, the doses to be used depend upon various conditions. Therefore, there are cases in which doses lower than or greater than the ranges specified above may be used.

In administering, the compounds of the present invention were administered as solid compositions, liquid compositions and other compositions for oral administration and injections, external compositions and suppositories etc. for parenteral administration.

Solid compositions for oral administration include compressed tablets, pills, capsules, dispersible powders, and granules. In such compositions, one or more of the active compound(s) is or are, admixed with at least one inert diluent (lactose, mannitol, glucose, hydroxypropylcellulose, microcrystalline cellulose, starch, polyvinylpyrrolidone, magnesium metasilicate aluminate etc.). The compositions may also comprise, as is normal practice, additional substances other than inert diluents: e.g. lubricating agents (magnesium stearate etc.), disintegrating agents (cellulose calcium gluconate etc.), and assisting agent for dissolving (glutamic acid, aspartic acid etc.) stabilizing agent (lactose etc.).

The tablets or pills may, If desired, be coated with a film of gastric enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable solutions, emulsions, suspensions, syrups and elixirs.

In such liquid compositions, one or more of the active compound(s) is or are used in inert diluent(s) commonly used in the art (purified water, ethanol etc.).

Besides inert diluents, such compositions may also comprise adjuvants such as wetting agents and suspending agents), sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfite etc.), isotonic buffers (sodium chloride, sodium citrate, citric acid etc.). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such Injections, one or more of active compound(s) is or are admixed at least one of inert aqueous diluent(s) (distilled water for injection, physiological salt solution etc.) or inert non-aqueous diluent(s)

(propylene glycol, polyethylene glycol, olive oil, ethanol, Polysorbate 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be usually sterilized by filtration (through a bacteria-retaining filter etc.), incorporation of sterilizing agents in the compositions or irradiation. After sterilizing as described, they also can be manufactured in the form of sterile solid compositions, for example, by freeze-drying, and which can be dissolved in sterile water or some other sterile diluents for injection immediately before use.

Other compositions for parenteral administration include liquids for external use, and endermic liniments (ointment etc.), suppositories and pessaries which comprise one or more of the active compound(s) and may be prepared by known methods.

REFERENCE EXAMPLES AND EXAMPLES

The following reference examples and examples are illustrate the present invention, but not limit the present invention.

The solvents in the parentheses show the developing or eluting solvents and the ratios of the solvents used are by volume in chromatographic separations.

Unless otherwise specified, "IR" were measured by liquid film method.

REFERENCE EXAMPLE 1

Synthesis of 2-Isopropyl-6-Phenylhexanoic Acid Methyl Ester

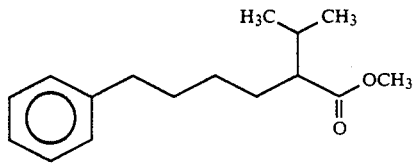

Diisopropylamine (0.881 ml) and HMPA (1.6 ml) were poured into THF (15 ml) and the solution was cooled to $-78°$ C. A 1.5N solution (3.9 ml) of n-butyl lithium in hexane was added to the mixture and the solution was stirred for 30 mins at $-78°$ C., moreover, a solution of 6-phenylhexanoic acid methyl ester (945 mg) in THF (10 ml) was dropped into the solution. The solution was stirred for 45 mins. A solution of 2-iodopropane (0.49 ml) in THF (5 ml) was added to the reaction solution. The solution was stirred with raising the temperature slowly overnight.

After the reaction solution was acidified (pH 3) with a mixture of ice-1N hydrochloric acid, the solution was extracted with ethyl acetate. The extract was washed with a saturated aqueous solution of sodium bicarbonate followed by saturated brine, dried and then evaporated. The residue was purified by column chromatography on silica gel to give the title compound (547 mg) having the following physical data:

TLC: Rf 0.52 (ethyl acetate:n-hexane = 1:19).

REFERENCE EXAMPLE 2

Synthesis of N-(2-isopropyl-6-phenylhexanoyl)-L-prolinol

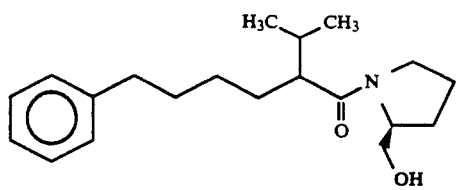

2-isopropyl-6-phenylhexanoic acid methyl ester (540 mg; prepared in reference example 1) was dissolved into ethanol (10 ml). A 3N aqueous solution of potassium hydroxide (4 ml) was added to the solution and stirred with refluxing overnight. The reaction mixture was concentrated. Ice-water was added to the residue and the solution was acidified with 1N hydrochloric acid. The solution was extracted with ethyl acetate. The separated ethyl acetate layer was washed with water, followed by saturated brine, dried and then evaporated. Toluene was added to the obtained residue. The solution was evaporated. The residue was dried. Oxalyl chloride was added to the residue. The solution was stirred for 20 mins. Toluene was added to the solution. The solution was concentrated and the residue was dried.

The residue was dissolved in methylene chloride (10 ml). 2-hydroxymethylpyrrolidine (0.28 ml) was added to the solution. The solution was cooled in an ice-bath. Triethylamine (0.42 ml) was added to the reaction solution. The mixture was stirred for 20 mins. Methylene chloride (30 ml) was added to the mixture. The methylene chloride layer separated was washed with a mixture of ice-1N hydrochloric acid, a saturated aqueous solution of sodium hydrocarbonate, followed by saturated brine, dried over magnesium sulfate and then evaporated.

The residue was purified by column chromatography on silica gel to give the title compound (504 mq) having the following physical data:

TLC: Rf 0.37 (ethyl acetate:n-hexane 1:1).

REFERENCE EXAMPLE 3

Synthesis of 2(R)-Formylcyclopentane-1-Carboxylic Acid Methyl Ester

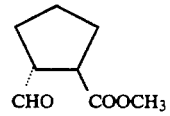

2(R)-hydroxymethylcyclopentane-1-carboxylic acid methyl ester (210 mg) was dissolved in DMSO (6 ml). Triethylamine (0.739 Ml) was added to the solution. A solution of sulfur trioxide-pyridine complex (422 mg) in DMSO (2 ml) was added to the solution. After 20 mins, ice was added to the reaction mixture. The mixture was diluted with ethyl acetate and water.

The water layer separated was extracted twice with ethyl acetate. The solution was washed with 1N hydrochloric acid, water, followed by an aqueous solution of sodium bicarbonate and dried over magnesium sulfate. Solvent was removed under reduced pressure to give the title compound (200 mg) having the following physical data:

TLC: Rf 0.64 (ethyl acetate:n-hexane = 1:2).

REFERENCE EXAMPLE 4

Synthesis of 2(S)-(4-Phenyl-1Z-Butenyl)Cyclopentanecarboxylic Acid Methyl Ester

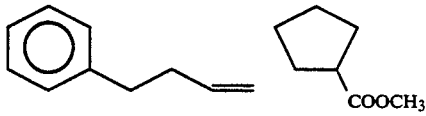

DMSO (1.5 ml) was added to sodium hydride (76 mg). The mixture was stirred for 1 hr. at 70° C. The solution (1.5 ml) of sodium hydride in DMSO aforesaid was dropped into a solution of triphenyl (3-phenylpropyl) phosphonium bromide (980 mg) in DMSO (5 ml). The solution was stirred. After 5 mins, a solution of 2(R)-formylcyclopentane-1-carboxylic acid methyl ester (200 mg; prepared in reference example 3) was added to the solution at once. The solution was stirred for 30 mins. The reaction mixture was poured into ice-water. The solution was extracted with ether twice. The ether layers separated were mixed. The solution was washed with water, followed by saturated brine, dried over magnesium sulfate and evaporated.

The residue was purified by column chromatography on silica gel to give the title compound (220 mg) having the following physical data:

TLC: Rf 0.53 (ethyl acetate:n-hexane = 1:9).

REFERENCE EXAMPLE 5

Synthesis of 2(R)-(4-Phenylbutyl)Cyclopentanecarboxylic Acid Methyl Ester

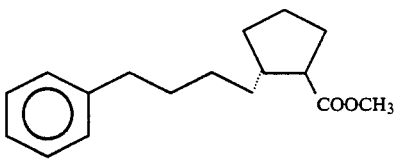

2(S)-(4-phenyl-1Z-butenyl)cyclopentanecarboxylic acid methyl ester (220 mg; prepared in reference example 4) was dissolved in ether (ml). Palladium carbon (100 mg; 5%) was added to the solution. The suspension was stirred for 1 hour under an atmosphere of hydrogen.

After the reaction, palladium carbon was filtered off by a glass filter. The filtrate was concentrated. The obtained residue was purified by column chromatography on silica gel to give the title compound (210 mg) having the following physical data:

TLC: Rf 0.58 (ethyl acetate:n-hexane = 1:9).

REFERENCE EXAMPLE 6

Synthesis of 2-Isopropyl-7-(P-Nitrophenyl)Heptanoic Acid

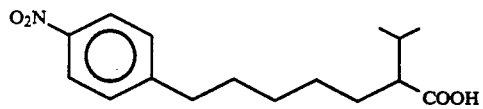

2-isopropyl-7-phenylheptanoic acid (1.0 g; prepared as the intermediate for the compound of example 1 (b)) was dissolved in anhydrous acetic acid (5 ml). The solution was cooled in an ice-bath. Fuming nitric acid (0.4 ml) was dropped into the solution. The solution was stirred for 30 mins. Anhydrous acetic acid was quenched by adding potassium hydroxide to the reaction solution. The reaction solution adjusted to pH 6.0~7.0 was extracted with ethyl acetate. The ethyl acetate layer separated was washed with water, followed by saturated brine, dried and then evaporated. The residue was purified by column chromatography on silica gel to give the title compound (850 mg) having the following physical data:

TLC; Rf 0.28 (ethyl acetate:n-hexane = 1:4).

REFERENCE EXAMPLE 7

Synthesis of N-[2-Isopropyl-7-(P-Nitrophenyl)Heptanoyl]-L-Prolinol

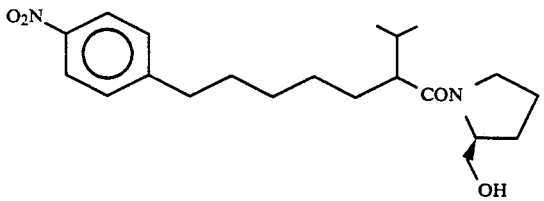

Oxalyl chloride (10 ml) was added to 2-isopropyl-7-(p-nitrophenyl)heptanoic acid (200 mg; prepared in reference example 6). The solution was stirred for 10 mins, and concentrated to dryness. Methylene chloride (10 ml) was added to this residue followed by the addition of 2-hydroxymethylpyrrolidine (0.087 ml). The solution was cooled with ice. Triethylamine (0.143 ml) was added to this reaction solution. The solution was stirred for 30 mins. Subsequently, the reaction solution was evaporated. The residue was purified by column chromatography on silica gel to give the title compound (150 mg) having the following physical data:

TLC: Rf 0.24 (ethyl acetate:n-hexane = 1:1).

EXAMPLE 1

Synthesis of N-(2-Isopropyl-6-Phenylhexanoyl)-L-Prolinal

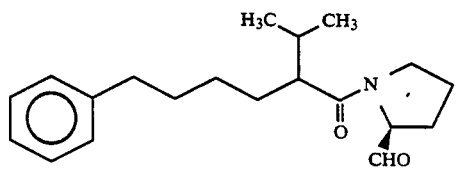

N-(2-isopropyl-6-phenylhexanoyl)-L-prolinol was dissolved in dry DMSO (1.5 ml). Triethylamine (0.35 ml) was added to this solution. A solution of sulfur trioxide-pyridine complex (414 mg) in DMSO (1 ml) was dropped to this solution. The solution was stirred for 10 mins and poured into water. The mixture was extracted with ethyl acetate. The oily layer was washed with 1N hydrochloric acid, a saturated aqueous solution of sodium hydrocarbonate, followed by saturated brine, dried and evaporated. The residue was purified by column chromatography on silica gel to give the title compound (150 mg) having the following physical data:

TLC: Rf 0.51 (ethyl acetate:n-hexane=1:1);

IR : $\nu$2950, 1730, 1630, 1440–1420, 1130, 755, 700 cm$^{-1}$.

EXAMPLE 1 (a)–1 (g)

Using as materials the compounds of the general formula:

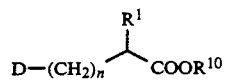

(wherein all of the symbols represent the same meaning as hereinbefore defined.) and the compounds of the general formula:

$$R^2-X \qquad (X)$$

(wherein all of the symbols represent the same meaning as hereinbefore defined), by the same procedure as described in reference example 1, reference example 2 and example 1, the compounds of the present invention shown in the following Table V were obtained.

TABLE V

| Example No. | Structural Formula | Name | Rf value (ethyl acetate:n-hexane) | IR |
|---|---|---|---|---|
| 1(a) | Ph-(CH$_2$)$_3$-CH(iPr)-CON-prolinal-CHO | N-(2-isopropyl-5-phenyl-pentanoyl)-L-prolinal | 0.32 (1:1) | $\nu$ 2950, 2850, 1725, 1620, 1440, 1420, 1330, 740, 690 cm$^{-1}$ |
| 1(b) | Ph-(CH$_2$)$_5$-CH(iPr)-CON-prolinal-CHO | N-(2-isopropyl-7-phenyl-heptanoyl)-L-prolinal | 0.4 (1:1) | $\nu$ 2910, 2840, 1720, 1620, 1420, 1320, 740, 690 cm$^{-1}$ |
| 1(c) | Ph-(CH$_2$)$_6$-CH(iPr)-CON-prolinal-CHO | N-(2-isopropyl-8-phenyl-octanoyl)-L-prolinal | 0.46 (4:6) | $\nu$ 2930, 1730, 1630, 1420 cm$^{-1}$ |
| 1(d) | Ph-(CH$_2$)$_7$-CH(iPr)-CON-prolinal-CHO | N-(2-isopropyl-9-phenyl-nonanoyl)-L-prolinal | 0.39 (1:2) | $\nu$ 1720, 1620, 1410, 740, 690 cm$^{-1}$ |
| 1(e) | Ph-(CH$_2$)$_8$-CH(iPr)-CON-prolinal-CHO | N-(2-isopropyl-10-phenyldecanoyl)-L-prolinal | 0.49 (1:1) | $\nu$ 2900, 2830, 1725, 1620, 1410, 740, 690 cm$^{-1}$ |
| 1(f) | Ph-(CH$_2$)$_5$-CH(iBu)-CON-prolinal-CHOl | N-(2-isobutyl-7-phenyl-heptanoyl)-L-prolinal | 0.22 (1:3) | $\nu$ 1720, 1620, 1410, 740, 690 cm$^{-1}$ |

| Example No. | Structural Formula | Name | Rf value (ethyl acetate:n-hexane) | IR |
|---|---|---|---|---|
| 1(g) | (structure: phenyl-(CH₂)₄-CH(CH₂-phenyl)-CON-pyrrolidine-CHO) | N-(2-benzyl-6-phenyl-hexanoyl)-L-prolinal | 0.45 (3:7) | ν 2925, 1725, 1625, 1490, 1440, 740, 690 cm⁻¹ |

EXAMPLE 1 (h)–1 (o)

Using as materials the compounds of the general formula:

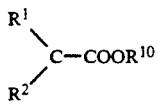

(V)

(wherein all of the symbols represent the same meaning as hereinbefore defined.) and the compounds of the general formula:

$$D-(CH_2)_n-$$ (XI)

(wherein all of the symbols represent the same meaning as hereinbefore defined), by the same procedure as reference example 1, reference example 2 and example 1, the compounds of the present invention shown in the following Table VI was obtained.

TABLE VI

| Example No. | Structural Formula | Name | Rf value (ethyl acetate:n-hexane) | IR |
|---|---|---|---|---|
| 1(h) | (structure with phenyl-(CH₂)₄, ethyl, CON-pyrrolidine-CHO) | N-(2-ethyl-6-phenyl-hexanoyl)-L-prolinal | 0.32 (1:1) | ν 3450, 2920, 1725, 1625, 1420, 1325 cm⁻¹ |
| 1(i) | (structure with phenyl-(CH₂)₄, cyclopentyl, CON-pyrrolidine-CHO) | N-(2-cyclopentyl-6-phenylhexanoyl)-L-prolinal | 0.44 (1:1) | ν 2930, 1730, 1625, 1420, 1310 cm⁻¹ |
| 1(j) | (structure with phenyl-(CH₂)₅, O-isopropyl, CON-pyrrolidine-CHO) | N-(2-isopropyloxy-7-phenylheptanoyl)-L-prolinal | 0.41 (2:1) | ν 3425, 1730, 1625, 1425, 1365, 1325, 1115 cm⁻¹ |
| 1(k) | (structure with phenyl-(CH₂)₅, phenyl, CON-pyrrolidine-CHO) | N-(2,7-diphenylheptanoyl)-L-prolinal | 0.35 (1:1) | ν 1730, 1635, 1415, 750, 700 cm⁻¹ |

TABLE VI-continued

| Example No. | Structural Formula | Name | Rf value (ethyl acetate:n-hexane) | IR |
|---|---|---|---|---|
| 1(l) | (phenyl)-(CH₂)₅-C(CH₃)₂-CON-pyrrolidine-CHO | N-(2,2-dimethyl-7-phenylheptanoyl)-L-prolinal | 0.37 (1:1) | ν 1725, 1610, 1395, 1360, 745, 695 cm⁻¹ |
| 1(m) | Et-(phenyl)-(CH₂)₅-CH(iPr)-CON-pyrrolidine-CHO | N-[2-isopropyl-7-(p-ethylphenyl)heptanoyl]-L-prolinal | 0.29 (1:2) | ν 1720, 1620, 1410 cm⁻¹ |
| 1(n) | CH₃O-(phenyl)-(CH₂)₅-CH(iPr)-CON-pyrrolidine-CHO | N-[2-isopropyl-7-(p-methoxy phenyl)heptanoyl]-L-prolinal | 0.38 (1:1) | ν 2900, 2840, 1720, 1615, 1500, 1450, 1410, 1235, 1160, 1020, 820, 740 cm⁻¹ |
| 1(o) | Cl-(phenyl)-(CH₂)₅-CH(iPr)-CON-pyrrolidine-CHO | N-[2-isopropyl-7-(p-chloro phenyl)heptanoyl]-L-prolinal | 0.38 (1:1) | ν 1725, 1625, 1485, 1420, 1085, 1010 cm⁻¹ |

EXAMPLE 2

Synthesis of N-[DL-Trans-2-(4-Phenylbutyl)Cyclopentanecarbonyl]-L-prolinal

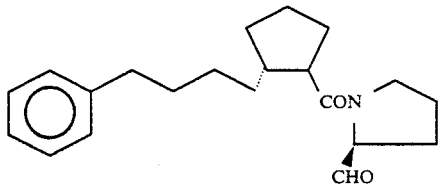

1(S)-4-phenyl-1-butylcyclopentanecarboxylic acid methyl ester (210 mg: prepared in reference example 5) was reacted by the same procedure as described in reference example 2 and example 1 to give the title compound having the physical data shown Table VII and the compound of example 2(a).

TABLE VII

| Example No. | Structural Formula | Name | Rf value (ethyl acetate:n-hexane) | IR |
|---|---|---|---|---|
| 2 | (phenyl)-(CH₂)₃-cyclopentyl-CON-pyrrolidine-CHO | N-[DL-trans-2-(4-phenylbutyl)cyclopentanecarbonyl]-L-prolinal | 0.44 (1:1) | ν 1720, 1620, 1410, 730, 690 cm⁻¹ |
| 2(a) | (phenyl)-(CH₂)₃-cyclohexyl-CON-pyrrolidine-CHO | N-[9-(4-phenylbutyl)cyclohexane carbonyl]-L-prolinal | 0.48 0.40 (1:1) | ν 2900, 2820, 1710, 1610, 1420, 1400, 730, 680 cm⁻¹ |

EXAMPLE 3

Synthesis of N-[2-Isopropyl-7-(P-Nitrophenyl)Heptanoyl]-L-Prolinal

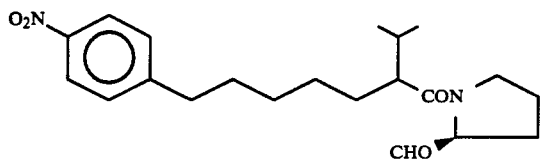

N-[2-isopropyl-7-(p-nitrophenyl)heptanoyl]-L-prolinol (150 mg: prepared in reference example 7) was treated by the same procedure as described in example 1 to give the title compound (78 mg) having the following physical data:

TLC: Rf 0.65 (ethyl acetate:n-hexane=4:1);
IR : $\nu$ 1720, 1620, 1500, 1410, 1330, 840, 730 cm$^{-1}$.

EXAMPLE 4 (a)–4 (b)

Using as materials the compounds of the general formula:

(wherein all of the symbols represent the same meaning as hereinbefore defined.) and the compounds of the general formula:

 (X)

(wherein all of the symbols represent the same meaning as hereinbefore defined), by the same procedure as described in reference example 1, reference example 2 and example 1, the compounds of the present invention shown in the following Table VIII was obtained.

TABLE VIII

| Example No. | Structural Formula | Name | Rf value (ethyl acetate:n-hexane) | IR |
|---|---|---|---|---|
| 4 | 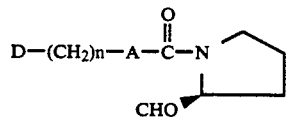 | N-[2-isopropyl-6-(2-naphthyl)hexanoyl]-L-prolinal | 0.27 (1:2) | $\nu$ 1720, 1620, 1420, 1160, 1130, 1230, 1030, 850, 810, 745 cm$^{-1}$ |
| 4(b) | 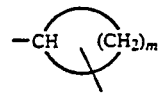 | N-[2-isopropyl-6-(1-naphthyl)hexanoyl]-L-prolinal | 0.30 (1:2) | $\nu$ 1720, 1620, 1410, 1230, 770 cm$^{-1}$ |

FORMULATION EXAMPLE

The following components were admixed in conventional method and punched out to obtain 100 tablets each containing 50 mg of active ingredient.

| | |
|---|---|
| N-[2-isopropyl-7-(p-nitrophenyl)heptanoyl]-L-prolinal | 5 g |
| Cellulose calcium gluconate (disintegrating agent) | 0.2 g |
| Magnesium stearate (lubricating agent) | 0.1 g |
| Microcrystaline cellulose | 4.7 g |

What is claimed is:

1. A prolinal derivative of the formula:

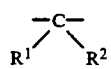 (I)

wherein A represents a group of the formula:

$$-\underset{\underset{R^2}{R^1}}{\overset{}{C}}-$$

wherein one of $R^1$ and $R^2$ represents a hydrogen atom and the other represents an alkyl group of from 2 to 5 carbon atoms, an alkoxy group of from 1 to 5 carbon atom(s), phenyl group, benzyl group, a cycloalkyl group of from 4 to 6 carbon atoms or a (cycloalkyl group of from 4 to 6 carbon atoms)-methyl group or $R^1$ and $R^2$, which are the same or different, each represents an alkyl group of from 1 to 4 carbon atom(s), or a group of the formula:

$$-CH\underset{}{\underbrace{\phantom{XX}(CH_2)_m}}$$

wherein m represents an integer of from 3 to 6, n represents an integer of from 3 to 10, D represents a heterocyclic ring selected from the group consisting of thiophene, pyridine, imidazole, indole, benzothiophene, and phenothiazine rings, which ring represented by D may be partially of fully saturated and wherein said ring represented by D is unsubstituted or substituted by from one to three of a halogen atom, a nitro group, a trifluoromethyl group, an alkyl or an alkoxy group of from 1 to 4 carbon atom(s).

2. The derivative according to claim 1, wherein one of $R^1$ and $R^2$ is a hydrogen atom and the other is an alkyl group of from 2 to 5 carbon atoms or $R^1$ and $R^2$, which are the same or different, each represents an alkyl group of from 1 to 4 carbon atom(s).

3. The derivative according to claim 1, wherein one of $R^1$ and $R^2$ is a hydrogen atom and the other is an alkoxy group of form 1 to 5 carbon atom(s).

4. The derivative according to claim 1, wherein one of $R^1$ and $R^2$ is a hydrogen atom and the other is a phenyl group, a benzyl group, a cycloalkyl group of from 4 to 6 carbon atoms, or a (cycloalkyl of from 4 to 6 carbon atoms)-methyl group.

5. The derivative according to claim 1, wherein A is a group of the formula:

wherein m has the same meaning as in claim 15.

6. A pharmaceutical composition for treating amnesia which comprises, as an active ingredient, an effective amount of the prolinal derivative of formula (I) depicted in claim 1 and a pharmaceutically acceptable carrier, coating, or both a carrier and a coating.

7. A method for treating amnesia which comprises administering a therapeutically effective amount of the prolinal derivative of formula (I) depicted in claim 1.

* * * * *